(12) United States Patent
Wetegrove et al.

(10) Patent No.: US 8,741,157 B2
(45) Date of Patent: Jun. 3, 2014

(54) BIOFOULING CONTROL

(75) Inventors: Robert L. Wetegrove, Winfield, IL (US); Andrew J. Cooper, Oswego, IL (US); Steven R. Hatch, Naperville, IL (US)

(73) Assignee: Nalco Company, Naperville, IL (US)

( * ) Notice: Subject to any disclaimer, the term of this patent is extended or adjusted under 35 U.S.C. 154(b) by 1130 days.

(21) Appl. No.: 12/179,949

(22) Filed: Jul. 25, 2008

(65) Prior Publication Data

US 2008/0279964 A1  Nov. 13, 2008

Related U.S. Application Data

(62) Division of application No. 11/259,790, filed on Oct. 27, 2005, now abandoned.

(51) Int. Cl.
| | |
|---|---|
| *C02F 1/76* | (2006.01) |
| *C02F 1/72* | (2006.01) |
| *C02F 1/68* | (2006.01) |
| *A62D 3/00* | (2007.01) |
| *C01B 11/00* | (2006.01) |
| *C11D 3/395* | (2006.01) |
| *C23F 11/00* | (2006.01) |
| *A61L 2/18* | (2006.01) |

(52) U.S. Cl.
USPC ............... 210/754; 210/167.01; 210/167.3; 210/752; 210/755; 210/756; 210/758; 210/764; 210/765; 252/186.36; 422/7; 422/37

(58) Field of Classification Search
USPC ............ 424/661, 723; 422/7, 37; 252/186.36; 210/752, 754, 755, 758, 756, 764, 765; 162/70, 74, 84, 87, 161
See application file for complete search history.

(56) References Cited

U.S. PATENT DOCUMENTS

| | | | | |
|---|---|---|---|---|
| 4,818,413 | A * | 4/1989 | Hoover et al. | 210/739 |
| 6,110,387 | A | 8/2000 | Choudhury et al. | |
| 6,478,972 | B1 * | 11/2002 | Shim et al. | 210/755 |
| 6,669,904 | B1 * | 12/2003 | Yang et al. | 422/37 |
| 7,459,075 | B2 * | 12/2008 | Burns et al. | 210/150 |
| 2007/0098817 | A1 * | 5/2007 | Wetegrove et al. | 424/661 |

FOREIGN PATENT DOCUMENTS

EP  0302501 A1 *  8/1989  ............ C02F 1/50

* cited by examiner

*Primary Examiner* — Jane C Oswecki

(74) *Attorney, Agent, or Firm* — Benjamin E. Carlsen

(57) ABSTRACT

A system and method for stabilizing bromine in an industrial water system by monitoring and flexible dosing of chlorine oxidant and halide ion stabilizer residual levels. The system comprises chlorine oxidant, and a halide ion source with a halogen stabilizer.

3 Claims, No Drawings

BIOFOULING CONTROL

CROSS REFERENCE TO RELATED APPLICATIONS

This application is a divisional application of U.S. patent application Ser. No. 11/259,790, which was filed on Oct. 27, 2005 now abandoned.

FIELD OF THE INVENTION

This invention is in the field of industrial water systems. Specifically, this invention optimizes the use of halogen biocides in industrial water systems.

BACKGROUND OF THE INVENTION

Fouling in industrial water systems occurs even in industrial water systems treated with the best water treatment programs currently available. When fouling occurs, the water system is negatively impacted by contamination including deposition of air-borne, water-borne and water-formed contaminants, process leaks, and other factors. If fouling is allowed to progress, the system can suffer from decreased operational efficiency, premature equipment failure, and increased health-related risks associated with microbial fouling.

Fouling can also occur due to microbial contamination. Sources of microbial contamination in industrial water systems are numerous and may include, but are not limited to, air-borne contamination, water make-up, process leaks, and improperly cleaned equipment. These microorganisms can establish microbial communities on any wetable or semi-wetable surface of the water system. More than 99% of the microbes present in the water process may be present on system surfaces.

The use of oxidizing biocides in biofouling control methods is well established. Common oxidizing biocides such as chlorine and bromine are effective biofouling control agents so long as they are maintained at effective concentrations in the water. Unless the concentrations of the biocides are effectively monitored, improper levels result in undesired microbial growth, scaling, corrosion, environmental impact, and increased cost that limit industrial applicability.

Developments in industrial water treatment incorporating higher pH values and corrosion inhibitors have driven interest in biocide systems other than chlorine. Bromine use in biofouling control usually occurs through addition of sodium bromide to the water system with an oxidizing agent such as chlorine gas or sodium hypochlorite. The result of this approach is the generation of hypobromous acid, which may require less biocide feed to maintain overall cleanliness than a comparable system operating on chlorine alone. However, many of the same compounds and conditions that reduce chlorine effectiveness also reduce bromine effectiveness.

U.S. Pat. No. 6,110,387 (hereinafter the '387 patent) entitled "SULFAMATE STABILIZATION OF A BROMINE BIOCIDE IN WATER" to Albemarle Corporation attempted to demonstrate the importance of manipulating the order of addition of active components to the water to be treated. Essentially, the '387 patent discloses effective biocidal activity is achieved by introducing sulfamate and water-soluble bromide to the system before the chlorine oxidant is added. Uncertainty of improved biocidal performance, cost-effectiveness, actual stabilization, and effects on the environment limit its application in biocidal control.

U.S. Pat. No. 6,478,972 entitled "Method of Controlling Microbial Fouling" to Acculab Co. discloses the use of hypobromous acid, HOBr, formed by the reaction between an aqueous solution of alkali or alkaline earth metal hypochlorite and a bromide ion source. The applicants describe aqueous hypochlorite solution, water-soluble bromide ion source, with sulfamate ion source as stabilizer as an improved antifouling system.

Despite ongoing research, an efficient strategy for feeding effective doses of bromide and stabilizer to water systems being treated with chlorine has not previously been described. Thus, the multiple problems in devising an efficient biofouling control system remain.

SUMMARY OF THE INVENTION

Effective and economical biofouling control is provided by the novel use of chlorine oxidant, a halide ion source, and a stabilizer characterized by independently controlled dosing of chlorine and bromide mixed with halogen stabilizer. The system is exemplified by the combined use of sodium sulfamate, bromide ion, and chlorine oxidant in the method described below.

Control of biofouling in industrial water systems comprises: (a) providing at least one or more means to independently monitor and control chlorine oxidant; (b) comparing the monitored concentration identified in step (a) to a predetermined concentration range according to the system to be treated; (c) adding chlorine oxidant at a rate and in an amount sufficient to maintain the determined biocidal effective range and, (d) adding stabilizer and halide ion source in amounts and rates sufficient to realize halogen levels sufficient to effect fouling control in said body of water.

The method controls microorganisms in industrial water systems by concurrent monitoring and flexible dosing of chlorine oxidant in the presence of a bromide ion source and sodium sulfamate at concentrations sufficient to provide free and stabilized halogen biocide. Such free and stabilized halogens include free chlorine, free bromine, chlorosulfamates, and bromosulfamates.

DETAILED DESCRIPTION OF THE INVENTION

Definitions

As used herein, the terms identified below are meant to designate the following:

"Halide Ion Source" includes the bromide ion sources ammonium bromide [ammonium bromide 38%, CAS 12124-97], sodium bromide [sodium bromide, CAS 7647-15-6], lithium bromide [lithium bromide, CAS 7550-35-8], calcium bromide [calcium bromide, CAS 7789-41-5], potassium bromide [potassium bromide, CAS 7758-02-3], bromine chloride [bromine chloride CAS 13863-41-7], bromine [bromine CAS 7726-95-6], BCDMH [3-Bromo-1-chloro-5,5-dimethylhydantoin, CAS 126-06-7], DBDMH [1,3-Dibromo-5,5-dimethylhydantoin CAS 77-48-5], DBNPA [2,2-Dibromo-3-nitrilopropionamide CAS 10222-01-2], Bronopol [2-Bromo-2-nitropropane-1,3-diol, CAS 52-51-7], and other effective bromide sources known to those skilled in the art.

"Chlorine Oxidant" means chlorine ($Cl_2$) [chlorine, CAS 7782-50-5], hypochlorous acid (HOCl), [hypochlorous acid, CAS 7790-92-3] or hypochlorite ion, (OCl) [hypochlorite, CAS 14380-61-1].

"Chlorine Oxidant Source" means a substance or mixture of substances releasing, generating, or yielding Chlorine Oxidant. Examples include gaseous or liquid chlorine sources, sodium hypochlorite [sodium hypochlorite, CAS 7681-52-9], calcium hypochlorite [calcium hypochlorite, CAS 7778-54-3], dichloro-isocyanurate [1,3-Dichloroisocyanuric Acid, CAS 2782-57-2], trichloro-isocyanurate, chlorosulfamate [chlorosulfamic acid, CAS 7778-42-9], BCDMH, dichloro-hydantoin [1,3-dichloro-5,5-dimethylhydantoin, CAS 118-52-5], or electrolytic chlorine generators.

"Halogen Stabilizer" includes sulfamic acid [Sulfamic acid, CAS 5329-14-6], sodium sulfamate [Sodium Sulfamate, CAS 13845-18-6], potassium sulfamate [Potassium Sulfamate, CAS 13823-50-2], saccharine [saccharin CAS 81-07-2], benzene sulfonamide [benzenesulfonamide, CAS 98-10-2], urea [urea CAS 57-13-6], ammonia [ammonia CAS 7664-41-7], thiourea [thiourea, CAS 62-56-6], creatinine [creatinine CAS 60-27-5], cyanuric acids [e.g. 1,3,5-triazine-2,4,6(1H,3H,5H)-trione, CAS 108-80-5], alkyl hydantoins [e.g. 2,4-Imidazolidinedione, CAS 461-72-3], monoethanolamine [1-amino-2-hydroxyethane CAS 141-43-5], diethanolamine [2,2'-dihydroxydiethylamine CAS 111-42-2], organic sulfonamides [e.g. sulfanilamide CAS 63-74-1], biuret [imidodicarbonicdiamide CAS 108-19-0], organic sulfamates, and melamine [1,3,5-triazine-2,4,6(1H,3H,5H) triimine CAS 108-78-1]

"Stabilized Halogen" includes chlorosulfamate [chlorosulfamate CAS 17172-27-9], dichlorosulfamate [dichlorosulfamate CAS 17085-87-9], bromosulfamate [bromosulfamate CAS 134509-56-1], dibromosulfamate, bromochlorosulfamate, and the bromo- and chloro-derivatives of the listed halogen stabilizers.

"Residual Oxidant" is Halogen capable of reacting with DPD [N, N-diethyl-p-phenylenediamine CAS 93-05-0] reagent "Chlorine Dose" is the amount of chlorine oxidant applied to the water system "Stabilizer Dose" is the amount of halogen stabilizer applied to the water system "Stabilized Bromine" is bromosulfamate, dibromosulfamate, bromochlorosulfamate, and the brominated derivatives of the defined halogen stabilizers.

"Biocidal Effective Range" is the concentration of oxidant required to mitigate pests in a treated water system.

"Biofouling" is undesirable sessile or planktonic organisms in a water system.

THE INVENTION

Halogen Stabilizer

Halogen Stabilizers are defined herein to include, but not limited to, sulfamic acid, sodium sulfamate, potassium sulfamate, saccharine, benzene sulfonamide, urea, ammonia, thiourea, creatinine, cyanuric acids, alkyl hydantoins, mono ethanolamine, diethanolamine, organic sulfonamides, biuret, organic sulfamates, and melamine. Exemplified halogen stabilizers include sulfamic acid or a water-soluble sulfamate salt. Examples of water-soluble sulfamate salts include but are not limited to sodium sulfamate or potassium sulfamate. The stabilizer concentration range is from about 0.01 to about 100 mg per liter. Illustrative ranges are about 0.1 to about 50 and about 1 to about 10 mg per liter.

Bromide ion Source

The bromide ion source is a water-soluble bromide salt. Examples of water-soluble bromide salts that may be used include sodium bromide, potassium bromide, calcium bromide, zinc bromide, ammonium bromide, lithium bromide, bromine chloride, bromine, BCDMH, DBDMH, DBNPA, Bronopol and the like. A water-soluble bromide salt is an alkali metal bromide or an alkaline earth bromide. Typically the alkali metal bromide includes the water-soluble bromide salt is sodium bromide. The bromide concentration range is from 0.1 to 1000 mg per liter. An illustrative range is about 30 to about 100 and about 1 to about 3 mg per liter.

Ratio of Stabilizer to Bromide Ion

The ratio of stabilizer to bromide ion is chosen to provide effective biofouling control while avoiding over-stabilization. This means a molar ratio of about 1 mole stabilizer to about 0.01 through about 100 moles of bromide ion. Illustrative molar ratios are about 1 mole stabilizer to about 1 through about 10 moles bromide ion. Inclusive in this range is a molar ratio in the range of about 1 mole stabilizer to about 1 through about 3 moles bromide ion.

Chlorine Oxidant

The chlorine dose and residual oxidant concentration will vary based on demand and the residual required to control biofouling. Residual oxidant concentrations should range from about 10 mg per liter to 0 mg per liter. Illustrative residual oxidant concentrations range from about 5 to about 0.1 mg per liter. A further illustrative range for residual oxidant concentrations range from about 2 mg per liter to about 0.2 mg per liter.

Monitoring Methods

Halogen oxidant monitoring methods include DPD, amperometric titration, FACS, Oxidation Reduction Potential (ORP), and the like.

Halide monitoring methods include ion chromatography, ion-selective electrodes, and various wet chemical methods known to those skilled in the art.

EXAMPLES

Comparative Example 1

A 27,000-gallon open recirculating cooling water system (pH 8.8) operating on a commercial building used a combination of sodium hypochlorite and sodium bromide as a biocide program. The chlorine oxidant and bromide were blended at a 4:1 $Cl_2$:Br molar ratio just prior to dosing into the cooling system. The chlorine oxidant and bromide combination was dosed to the cooling water system to maintain approximately 0.1 mg/L residual oxidant, controlled using a Hach CL17 chlorine analyzer (Hach Company, Loveland, Colo.).

Although microbial control was acceptable using this program, bromide concentrations in the cooling system water were not cost-effective on the low chlorine demand and low chlorine dose required for biofouling control in this water system.

To improve the biocide treatment efficiency of this cooling water system, a 30% sodium bromide and 10% sodium sulfamate solution replaced the former sodium bromide product. The 30% bromide and 10% sodium sulfamate solution was dosed directly to the cooling water system to maintain bromide and sulfamate concentrations in the cooling water of approximately 0.3 mg/L and 0.1 mg/L, respectively. Dosage of the bromide and sulfamate solution was controlled by a Nalco TRASAR® (Nalco Company, Naperville, Ill.) product controller. Sodium hypochlorite was added directly to the water system as needed to maintain a 0.1 mg/L residual oxidant, controlled using a Hach CL17 chlorine analyzer.

To measure the biofouling control performance of the new product and dosing method, total aerobic bacteria, anaerobic bacteria, fungi, and other microbes were measured using culture and microscopic analysis of water samples collected twice per week. Bromide and sulfamate concentrations from water samples were also measured twice per week using ion chromatography.

Bacterial counts were maintained at or below 10,000 CFU/ml during the test period. Fungi and anaerobic bacteria including, sulfate-reducing bacteria, were maintained below detection (<10 CFU/ml). Algae growth was controlled as assessed by visual inspection of sunlit areas.

The improved process and biofouling system, which incorporated sodium bromide and sodium sulfamate to maintain 0.3 mg/L bromide and 0.1 mg/L sulfamate in the cooling water system, illustrated that the bromide concentration in the water system was reduced by up to 99% while maintaining satisfactory control of biofouling.

Example 2

Controlled tests were also performed to determine the effect of sodium bromide and sodium sulfamate solutions on chlorine oxidant consumption, oxidant-induced corrosion, and oxidation-reduction control in chlorinated cooling water systems.

A 50-liter pilot cooling water system (pH 7.5) was treated with three different halogen oxidant methods:
1. sodium hypochlorite (NaOCl) only
2. NaOCl and sodium bromide (NaBr)
3. NaOCl and NaBr plus sodium sulfamate Sodium hypochlorite was dosed and controlled independently from the sodium bromide or sodium sulfamate dosing.

In each case, chlorine oxidant dose was controlled using an oxidation-reduction potential (ORP) meter at a 500 millivolt set point (GLI International, Milwaukee, Wis.). Sodium hypochlorite product consumption was measured by determining the use rate of a sodium hypochlorite product of known chlorine concentration. Sodium bromide and sodium sulfamate solution dosing was controlled by a Nalco TRASAR® (Nalco Company, Naperville, Ill.) product controller to maintain approximately 3 mg/L bromide and 1 mg/L sulfamate in the water system.

Table 1 shows chlorine oxidant consumption for each treatment strategy. Chlorine oxidant consumption is expressed as mg of chlorine oxidant dosed per liter of cooling water blowdown. The addition of sodium bromide to the cooling water system reduced chlorine oxidant consumption 36%. The addition of sodium bromide and sodium sulfamate to the cooling water system reduced chlorine oxidant consumption an additional 18% (total of 54% reduction) compared to the sodium bromide alone.

TABLE 1

| Oxidant Program | Chlorine Oxidant Consumption (mg/L) | Percent Chlorine Oxidant Savings |
|---|---|---|
| NaOCl only | 3.9 | — |
| NaOCl and NaBr | 2.5 | 36 |

TABLE 1-continued

| Oxidant Program | Chlorine Oxidant Consumption (mg/L) | Percent Chlorine Oxidant Savings |
|---|---|---|
| NaOCl and NaBr with sodium sulfamate | 1.8 | 54 |

Copper corrosion rates in the treated water system were measured using a Nalco NCM100 Corrosion Monitor (Nalco Company, Naperville, Ill.). Using only sodium hypochlorite for treatment, copper corrosion rates ranged from 0.15 to 0.28 mpy (mils per year). When sodium bromide and sodium sulfamate were added to this water system under independent dosing control, copper corrosion rates decreased to the range of 0.00 to 0.01 mpy.

"Although the invention has been described in detail in the foregoing for the purpose of illustration, it is to be understood that such detail is solely for that purpose and that variations can be made therein by those skilled in the art without departing from the spirit and scope of the invention except as except as it may be limited by the claims."

What is claimed is:

1. A method for control of biofouling in an industrial water system comprising copper surfaces, the method including the steps of:
    (a) concurrently monitoring in an industrial water system both a chlorine oxidant concentration and a concentration of sodium sulfamate;
    (b) providing a chlorine oxidant source;
    (c) providing a mixture of sodium sulfamate and bromide ion source the molar ratio of sodium sulfamate to bromide ion source in the mixture being within the range of 1:1 to 1:4;
    (d) comparing the monitored chlorine oxidant concentration to a pre-determined chlorine oxidant concentration known to function as an effective biocide in the industrial water system and appropriately adding the chlorine oxidant source at a rate and in an amount sufficient to achieve at least the pre-determined chlorine oxidant concentration, said pre-determined chlorine oxidant concentration being within the range of between 2 mg/liter and 0.2 mg/liter and;
    (e) comparing the monitored concentration of sodium sulfamate to a predetermined concentration of sodium sulfamate and bromide, source mixture known to effectively control foulant in the industrial water system and appropriately adding the mixture of sodium sulfamate and bromide ion source in an amount sufficient to achieve at least the pre-determined sodium sulfamate concentration between 0.01 mg/liter to 100 mg/liter, the adding to the water system of the mixture of sodium sulfamate and bromide ion source being independent of whether chlorine oxidant is being concurrently added to the system;
    wherein corrosion in the copper surfaces occurs at a rate which is at least 15 times slower to about 28 times slower than would occur were at least the same amount of sodium sulfamate added to the system in the absence of the bromide ion source.

2. The method of claim 1 in which the monitoring is accomplished by oxidation reduction potential.

3. The method of claim 1 in which the chlorine oxidant is sodium hypochlorite.

* * * * *

UNITED STATES PATENT AND TRADEMARK OFFICE
CERTIFICATE OF CORRECTION

PATENT NO.        : 8,741,157 B2
APPLICATION NO.   : 12/179949
DATED             : June 3, 2014
INVENTOR(S)       : Robert L. Wetgrove et al.

Page 1 of 1

It is certified that error appears in the above-identified patent and that said Letters Patent is hereby corrected as shown below:

In the Claims, Claim 1 item (e) at column 6 line 44 remove "," between bromide and source and replace with "ion".:

Signed and Sealed this
Third Day of November, 2015

Michelle K. Lee
*Director of the United States Patent and Trademark Office*